(12) United States Patent
Aizel et al.

(10) Patent No.: US 9,364,795 B2
(45) Date of Patent: Jun. 14, 2016

(54) NANO AND MICROFLUIDIC DEVICE FOR SEPARATING AND CONCENTRATING PARTICLES PRESENT IN A FLUID

(71) Applicant: COMMISSARIAT A L'ENERGIE ATOMIQUE ET AUX ENE ALT, Paris (FR)

(72) Inventors: Koceila Aizel, Antony (FR); Yves Fouillet, Voreppe (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 485 days.

(21) Appl. No.: 13/728,282

(22) Filed: Dec. 27, 2012

(65) Prior Publication Data
US 2013/0175171 A1    Jul. 11, 2013

(30) Foreign Application Priority Data

Dec. 27, 2011    (FR) ...................................... 11 62468

(51) Int. Cl.
*B01D 57/02*    (2006.01)
*B01L 3/00*    (2006.01)
(Continued)

(52) U.S. Cl.
CPC .............. *B01D 57/02* (2013.01); *B01D 61/427* (2013.01); *B01L 3/502753* (2013.01); *B01L 3/502761* (2013.01); *G01N 27/44743* (2013.01);
(Continued)

(58) Field of Classification Search
CPC ..................... G01N 27/447; B01L 2300/0681; B01L 2300/0896; B01L 3/502; B01D 61/427; B01D 57/02
See application file for complete search history.

(56) References Cited

U.S. PATENT DOCUMENTS

| 5,585,011 A | 12/1996 | Saaski et al. |
| 5,617,632 A | 4/1997 | Saaski et al. |
| 5,660,728 A | 8/1997 | Saaski et al. |

(Continued)

FOREIGN PATENT DOCUMENTS

| FR | 2 952 628 A1 | 5/2011 |
| WO | WO 97/47370 A1 | 12/1997 |

(Continued)

OTHER PUBLICATIONS

Steinle, et al. (Analytical Chemistry, 74: 2416-2422 (2002).*

(Continued)

*Primary Examiner* — Jennifer Dieterle
(74) *Attorney, Agent, or Firm* — Oblon, McClelland, Maier & Neustadt, L.L.P.

(57) ABSTRACT

A device for separating and concentrating particles present in a fluid, including: a first microchannel, having at least one first aperture; and at least one second microchannel, having at least one second aperture, and an end is disclosed. The first microchannel surrounds part or all of the second microchannel at the end. The first microchannel and the second microchannel are connected, at the end, by at least one nanochannel, the nanochannel(s) forming a restriction between the first microchannel and the second microchannel. A cap bounds the first microchannel, the second microchannel and the nanochannel at the end. The first microchannel and the second microchannel are made in a first substrate. The first aperture and the second aperture open into a same face of this substrate. The device may be used for separating and concentrating particles of biological samples, such as viruses, DNA or synthesic molecules.

27 Claims, 20 Drawing Sheets

(51) Int. Cl.
  *B01D 61/42* (2006.01)
  *G01N 27/447* (2006.01)

(52) U.S. Cl.
  CPC .. *B01L2300/0681* (2013.01); *B01L 2300/0896* (2013.01)

(56) References Cited

U.S. PATENT DOCUMENTS

| | | | |
|---|---|---|---|
| 5,697,153 | A | 12/1997 | Saaski et al. |
| 5,702,618 | A | 12/1997 | Saaski et al. |
| 5,705,070 | A | 1/1998 | Saaski et al. |
| 5,798,042 | A | 8/1998 | Chu et al. |
| 5,839,467 | A | 11/1998 | Saaski et al. |
| 5,938,923 | A | 8/1999 | Tu et al. |
| 6,044,981 | A | 4/2000 | Chu et al. |
| 8,603,413 | B2 | 12/2013 | Fouillet |
| 2002/0043638 | A1* | 4/2002 | Kao et al. ............ 251/129.06 |
| 2004/0011650 | A1* | 1/2004 | Zenhausern et al. ......... 204/547 |
| 2005/0023156 | A1* | 2/2005 | Ramsey et al. ............ 205/792 |
| 2006/0180469 | A1* | 8/2006 | Han et al. ............ 204/601 |
| 2007/0027383 | A1* | 2/2007 | Peyser et al. ............ 600/347 |
| 2007/0090026 | A1* | 4/2007 | Han et al. ............ 209/2 |
| 2008/0241962 | A1* | 10/2008 | Wang ............ 436/514 |
| 2009/0136948 | A1* | 5/2009 | Han et al. ............ 435/6 |
| 2009/0214392 | A1* | 8/2009 | Kameoka et al. ............ 422/102 |
| 2010/0000620 | A1* | 1/2010 | Fouillet et al. ............ 137/827 |
| 2010/0295415 | A1 | 11/2010 | Despesse et al. |
| 2011/0104025 | A1 | 5/2011 | Fouillet |
| 2011/0198225 | A1 | 8/2011 | Kim et al. |
| 2012/0224981 | A1 | 9/2012 | Fouillet et al. |

FOREIGN PATENT DOCUMENTS

| | | |
|---|---|---|
| WO | WO 98/46325 A1 | 10/1998 |
| WO | WO 2006/081270 A2 | 8/2006 |
| WO | WO 2006/081270 A3 | 8/2006 |

OTHER PUBLICATIONS

U.S. Appl. No. 14/406,795, filed Dec. 10, 2014, Marchalot, et al.
U.S. Appl. No. 14/114,009, filed Oct. 25, 2013, Fouillet, et al.
U.S. Appl. No. 14/138,514, filed Dec. 23, 2013, Renaudot, et al.
Preliminary Search Report issued Aug. 10, 2012 in French Patent Application No. 1162468.
Mark N. Hamblin, et al., "Selective Trapping and Concentration of Nanoparticles and Viruses in Dual-Height Nanofluidic Channels" The Royal Society of Chemistry, Lab on a Chip, vol. 10, 2010, pp. 173-178.
Samuel M. Stavis, et al., "Nanofluidic Structures with Complex Three-Dimensional Surfaces" Nanotechnology, vol. 20, No. 165302, 2009, 7 Pages.
Samuel M. Stavis, et al., "Separation and Metrology of Nanoparticles by Nanofluidic Size Exclusion" The Royal Society of Chemistry, Lab on a Chip, 2010, 4 Pages.
Elizabeth A. Strychalski, et al., "Non-planar Nanofluidic Devices for Single Molecule Analysis Fabricated Using Nanoglassblowing" Nanotechnology, vol. 19, No. 315301, 2008, 8 Pages.

\* cited by examiner

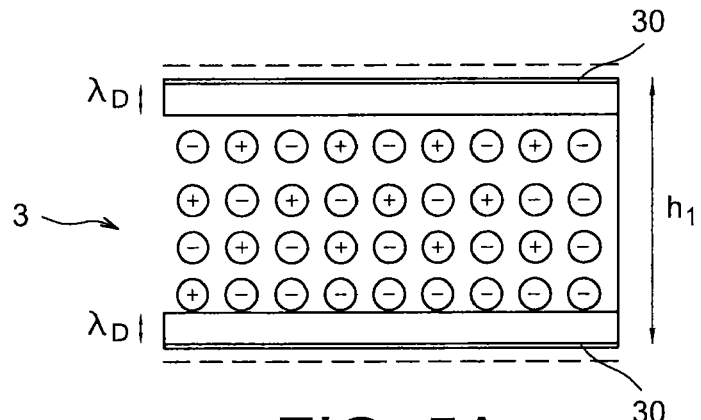
FIG. 5A
Background Art
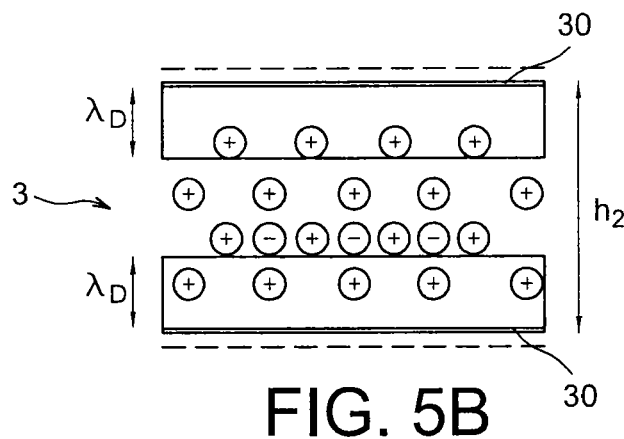
FIG. 5B
Background Art
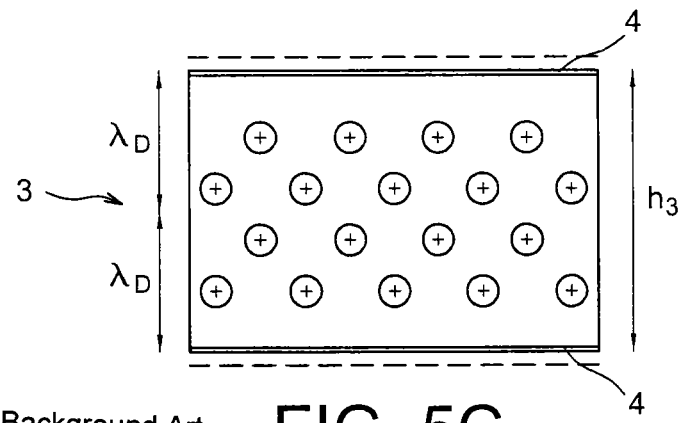
Background Art FIG. 5C

NANO AND MICROFLUIDIC DEVICE FOR SEPARATING AND CONCENTRATING PARTICLES PRESENT IN A FLUID

TECHNICAL FIELD

The invention relates to a device for separating and concentrating particles present in a fluid.

More precisely, the invention is connected with separating and concentrating particles present in a fluid by passing from at least one microchannel through at least one nanochannel by implementing a selective steric filtration and/or ionic filtration.

It is herein specified that within the scope of the invention, by microchannel, it is meant a fluidic channel having a height in a micrometre range, that is typically a channel the height of which or in other words the depth of which is in the order of few tens µm (micrometres). Typically also, a microchannel has a width in the order of about fifty to about one hundred µm (micrometres).

It is also herein specified that within the scope of the invention, by nanochannel, it is meant a fluidic channel having a height or in other words the depth, in the nanometre range, that is typically a channel the height of which is lower or equal to 100 nm (nanometres).

It is specified that within the scope of the invention, by particles, it is meant nanoparticles but also microparticles. By nanoparticles, it is meant generally (but not only) spherical particles the unit average diameter of which is lower than about 100 nm, in accordance with ISO TS/27687 standard. Advantageously, the size of particles intended to be separated and concentrated by the device according to the invention can be a few tens to about one hundred nanometres, typically between 50 and 120 nm. The same dimensions are indeed representative of some biological particles such as viruses, DNA as well as some particles developed for medical imaging applications.

PRIOR ART

To concentrate and separate particles present in a fluid, it is known that it is theoretically possible to use the steric effect as such and thus to pass the fluid through a nanochannel the manufacture of which is known.

But, it is also set that at the micro and nano-fluidic scale, fluid flow control can turn out to be difficult. Thus, since dimensions of nanochannels are lower than about one hundred nanometres, hydraulic resistance to be considered are very high. Thus, if it is attempted to pass directly a fluid from a microchannel to a nanochannel by hydrodynamic injection, very high pressures should be provided to achieve flow rates $Q_1$ which will always remain very low, in the order of a few nanolitres per minute (nl/min).

It is specified that by hydrodynamic injection, it is herein meant and within the scope of the invention, a fluid injection in a fluidic circuit only through application of a pressure difference (overpressure, suction or gravity) between the inlet and the outlet of the circuit.

It is specified as well that by electrokinetic injection, it is meant a fluid injection through application of an electrical voltage in a fluid circuit, in order to enable electrically charged species present in the circuit to be moved under the effect of the electrical field thus created with travelling speeds which are a function of their charges. The technique used can be electroosmosis or electrophoresis.

Thus, in an hydrodynamic injection mode, very long times are required to pass volumes of a few millilitres (ml). Such a configuration is schematically shown in FIG. 1: to pass a fluid from the inlet microchannel 1 to the outlet microchannel 2 through the nanochannel 3, it is necessary to apply much higher pressures P1 in the inlet microchannel 1 than those P2 in the outlet microchannel 2. Further, air bubble can be trapped, making filling of the nanochannel 3 even more difficult. Finally, particles present in the fluid can build up at the inlet of the nanochannel 3 and consequently start to clog the same.

To overcome these difficulties, systems which are commonly designated as "by-pass" devices and which are regularly found in literature have been proposed.

Such a by-pass device is schematically shown in FIG. 2: it consists of two microchannels 1, 2 parallel to each other and connected to each other by one or more nanochannel(s) 3, each microchannel 1, 2 being connected to a fluid inlet 10, 20 and an outlet 11, 21. In other words, the fluid flows through each microchannel 1 or 2 from its inlet 10 or 20 respectively at a given pressure P1 or P3 respectively up to its outlet 11 or 21 respectively at a pressure P2 or P4 respectively, and with a flow rate Q in the order of a few microliters per minute (µl/min). The fluid also flows through the nanochannel(s) 3 with a flow rate $Q_1$ in the order of a few nl/min by being by-passed from the microchannel 1 to the microchannel 2. Such a known by-pass device is advantageous in that it enables the handling, via the microchannels 1, 2, of liquid volumes that are greater and with a higher flow rate (Q in the order of several µl/min). The nanochannels can thus be more easily filled and possible air bubbles can be more easily purged without having to apply huge pressures. On the other hand, such a by-pass device has a number of drawbacks that can be summarized as follows:

the height of nanochannels 3 is fixed and determined during technological manufacturing steps;

small leaks are sufficient to destabilize the system. Thus, for example, if a stable flow $Q_1$ is desired to be induced in the nanochannels 3 by applying identical pressures ($P_1=P_2$) at both ends 10 and 11 of one of the microchannels 1, which then are both inlets, as symbolized in FIG. 3, thus a mere leak is likely to generate pressure fluctuations ($P_1 \neq P_2$) in turn likely to destabilize the flow $Q_1$ through the nanochannels 3.

In US patent application 2011/0198225, it is known another by-pass device consisting of the junction of microchannels between each other via one or more nanochannels. An electrical potential difference is applied to the ends of the microchannel, called sampling microchannel, through which flows the fluid to be sampled, whereas the microchannels, called buffer microchannels, in parallel to the sampling microchannel and connected thereto by the nanochannels, and wherein a buffer fluid is present, are grounded. An unique depletion area is thus created at the sampling microchannel which acts as an electrostatic barrier to any type of electrically charged species.

The physical phenomenon thus exploited is called Ion Concentration Polarization (ICP). This physical phenomenon will be reminded herein in reference to FIGS. 4 to 6D.

It is specified that in these figures, negatively charged ionic species are symbolized by a negative sign whereas those positively charged are symbolized by a positive sign.

First, the superimposition principle of the so-called Debye double layer will be reminded, in the vicinity of a substrate 30. As represented in FIG. 4, a buffer solution S wherein positive and negative ions are present comes to take on the wall of the substrate 30, of silica in FIG. 4 (species SiO⁻), according to a Debye double layer C1, C2 having a total thickness noted λd.

A first ion layer $C_1$ having a first opposite polarity (positive in the example represented) to that of ionic species present at the surface, settles in the vicinity of said surface. A second layer C2 is formed, comprising mobile ionic species. The second layer C2 includes ions, of said first polarity, which migrate to the vicinity of the first layer C1. It also includes ions of the opposite (negative) polarity, to balance the charge. This first layer C1 is used to screen the surface potential (herein negative), which screening is completed by the second layer C2. This double layer, called the Debye double layer has a thickness λd, which varies as a function of the solution salinity.

The thickness of a Debye double layer ranges from 1 nm to about one hundred nanometres depending on the buffer liquid S considered. Indeed, the lower the buffer liquid salinity, the higher the thickness of the Debye double layer. Thus, if a fluidic channel has at least one of its dimensions in the order of the dimensions of the Debye double layer, then the double layers of the channel can be superimposed and this channel becomes selective to a type of ion (anion or cation) depending on the surface charge of the material considered. Indeed, under these conditions, the surface charge becomes prevalent and will then repel ions having the same charge and attract ions having an opposite charge. An electrostatic phenomenon of ionic selective permeability is thus herein highlighted, known as "ion perm-selectivity". This ionic selective permeability phenomenon can be obtained by either reducing the height of the fluidic channel to reach thicknesses of Debye double layers or decreasing the buffer liquid salinity so that the thickness of the Debye double layer can reach the channel height. In FIGS. 5A to 5C, there are symbolized three situations of channel heights or salinities in a channel 40 formed between two substrates 30 negatively charged in surface, that is in a cation permeable channel: the height of the channel 3 is decreasing from FIG. 5A to FIG. 5C ($h_1 > h_2 > h_3$). This could also be the case of the buffer liquid salinity. In the situation of FIG. 5C, the ionic selective permeability is reached because the height $h_3$ of the channel 3 is equal to 2*λd, that is the thickness of two Debye double layers superimposed over each other. Typically, for a channel 3 bounded by two substrates 30 of silica and being in contact with a deionized water buffer liquid, one of the dimensions of the channel (height $h_3$) should be lower than or equal to about 100 nm.

The ICP phenomenon will now be described in reference to FIGS. 6A to 6D for deionized water at the junction between one or more nanochannels 3 and two microchannels 1, 2, wherein the ionic selective permeability can be reached in the nanochannel 3. The height $h_3$ of the nanochannel is thus in the order of 100 nm. It is specified that the channel 3 and the microchannels 1, 2 are made in silica substrates: without the application of an electrical field.

FIG. 6A represents a cation permeable nanochannel, communicating with two microchannels being upstream and downstream of the microchannel respectively. When an electrical field is applied between the inlet and the outlet of the nanochannel (FIG. 6B), cations are pumped through the nanochannel towards the cathode. Gradually, in the vicinity of the ends $Z_N$, the electroneutrality is locally broken (FIG. 6C).

To restore electroneutrality, an ionic depletion area or depletion area $Z_d$ is formed on the anode side, whereas an ionic enrichment area $Z_E$ appears at the cathode.

Hence, any further electrical charge delivery is thus prevented in order to keep electroneutrality in the depletion area $Z_d$. In other words, the depletion area $Z_d$ is an electrostatic barrier. It goes without saying that if the channel surfaces are of positive surface electric charge, the nanochannel 3 would be selective to anions and the phenomenon just described would have been geographically reversed and the depletion and enrichment areas would have been located on the cathode and anode side respectively.

This depletion area can act as a concentrator for any charged particle.

Thus, to come back to abovementioned US application 2011/0198225, the electrostatic barrier defined is implemented to amplify pumping of a liquid, control the liquid flow and desalt sea water. It is also provided in this patent application to deviate white blood cells present in human blood diluted with sea water. Once again, as in a by-pass device illustrated in FIGS. 2 and 3, the height of nanochannels is fixed and determined during manufacturing technological steps.

Publication [1] also describes a by-pass device enabling polystyrene nanoparticles as well as blood virus (Herpes and Hepatitis B) the unit size of which ranges from 30 to 120 nm to be filtrated, separated and sterically concentrated. In FIGS. 7A and 7B are reproduced illustrations of the device such as given in the publication. The device disclosed in this publication [1] consists of two microchannels 1, 2 parallel to each other and connected between each other by a number in the order of about one hundred nanochannels 3 parallel to each other. Each nanochannel 3 is made with a restriction as a tilted face: thus, the height of the nanochannel 3 switches from a height $h_1$ to a height $h_3$ (the other dimensions being otherwise indicated in FIG. 7A). Thus, an analyte as nanoparticles present in a buffer liquid is introduced into the inlet 10 of the microchannel 1, is trapped in the trapping area Zp defined by the tilted face, the buffer liquid on the other hand is discharged or evaporated to the outlet 20 of the outlet microchannel 2. If the analyte is marked by a fluorescent substance, it can then emit a fluorescent signal F when it is concentrated in the trapping area Zp, as symbolized by arrows F in FIG. 7B. In other words, the trapping area Zp can make up a full detection area. It appears upon reading the publication [1] that the entire device is made according to a sacrificial layer technology. The drawbacks of such a by-pass device can be listed as follows:

it is quite possible to have a clogging of nanochannels 3 at their restrictions Zp;

dead volumes at the microchannels 1, 2 are likely to generate a dramatic loss of analytes to be detected;

filling the channels through capillarity indicated in the publication unavoidably restricts the filling flow rate;

the manufacturing method is complex.

It is also known from publication [2], a by-pass device comprising a nanochannel 3 having an inner pyramidal shape with a continuous gradient of a height from about $h_0$ in the order of 10 nm to $h_1$ in the order of 500 nm through $h_3$ in the order of 100 nm. This device represented in FIG. 8 allows the steric separation depending on the size of polystyrene nanoparticles, along the nanochannel height gradient. This device enables metrology of said nanoparticles to be carried out. It also enables a gradual lengthening of DNA molecules to be created into the height gradient nanochannel by an entropy decreasing effect, the containment areas of the DNA molecules thus lengthened being located at the lowest heights of the nanochannel (between $h_0$ and $h_3$ in FIG. 8). The drawbacks of such a by-pass device can be listed as follows:

the lithography manufacturing method is complex and leaves behind roughnesses having a size of about 15 nm, that is having a not inconsiderable size that can generate adsorption phenomena and uncertainties about the effective nanochannel height;

the operation of the device can only be ensured according to an electrokinetic injection mode because pressures to be applied into the nanochannel would be too high according to a hydrodynamic injection mode.

The purpose of the invention is thus to provide a new device for separating and concentrating particles present in a fluid which overcomes part or all of the drawbacks of abovementioned prior art.

A particular purpose of the invention is to provide a new device for separating and concentrating particles of biological samples, such as viruses, DNA or synthetic molecules, particularly intended for medical imaging applications.

Another particular purpose of the invention is to provide a new device for separating and concentrating particles present in a fluid which further enables a better optical detection to be achieved than devices according to prior art, in particular the one disclosed in publication [1], when particles to be detected are marked by a fluorescent substance.

DISCLOSURE OF THE INVENTION

To do this, one object of the invention is a device for separating and concentrating particles present in a fluid, comprising:
- a first microchannel, having at least one first aperture;
- at least one second microchannel, having at least one second aperture, and an end;
- the first microchannel surrounding at least part (or part or all) of the second microchannel at said end;
- the first microchannel and the second microchannel are connected, at said end, by at least one nanochannel, the nanochannel forming a restriction between the first microchannel and the second microchannel;
- a cap bounding the first microchannel, the second microchannel and the nanochannel at said end.

The first microchannel and the second microchannel are preferably made in a first substrate, said first aperture and said second aperture opening into a same face, or on a same side, of this substrate. In particular, this configuration makes the manufacture of the device easier.

Yet preferably, the geometry of the microchannel is fixed during a predetermined time period.

According to one embodiment, the first microchannel and the second microchannel are made in a first substrate, whereas the cap is made in a second substrate, assembled with the first substrate, the nanochannel being bounded by a space between the first and second substrates.

The first microchannel can have two first apertures. The second microchannel can have a single second aperture. Thus, a device according to the invention can be made with a number of three fluidic inlets/outlets.

According to one embodiment, the restriction between the first and second microchannels is spatially distributed according to a closed annular or polygonal geometry, the connection between the first and second microchannels being made by one or more nanochannels distributed according to this geometry.

According to one embodiment, the device can then further comprise a plurality of block-forming extra heights distributed evenly spaced inside the restriction, said blocks being of a height $h_3$ at most equal to that of the restriction, two adjacent blocks bounding a nanochannel. The blocks can be of a height $h_3$ substantially equal to that of the restriction formed by the nanochannels and are sealed to the cap and thus make up sealing blocks. Alternatively, the blocks can be of a height $h_3$ lower than that of the restriction formed by the nanochannels and are not sealed to the cap.

Advantageously, the cap is adapted to be able to be flexurally strained under the action of an actuator, while being kept fixed during a determined time period. The actuator can be at least one electromechanical actuator attached to the upper face of the cap to flexurally strain it. The electromechanical actuator is then preferably a piezoelectric element. It can also be the fluid itself which, by depression or overpressure in one of the microchannels, is likely to flexurally strain the cap.

According to one advantageous embodiment, the device can comprise at least two restrictions formed by one or more nanochannels having a closed annular or polygonal shape, part or all of which can be for example concentrically arranged with respect to one another around a single second microchannel. The height $h_3$ of one of both restrictions formed by one or more nanochannels can be different from the height $h_4$ of the other of both restrictions formed by one or more nanochannels.

According to one embodiment, the device can comprise at least two second microchannels and at least two restrictions formed by one or more nanochannels having a closed annular or polygonal shape, part or all of each nanochannel being arranged around a single second microchannel.

Advantageously, the portion at the end of the second microchannel and the portion of the cap adjacent to the nanochannel can be provided to be functionalized by the presence of ligands secured to their surface by a silylated function in order to capture particles concentrated at said portions.

Thus, the device for separating and concentrating particles is designed according to an architecture clearly distinct from abovementioned by-pass type devices according to prior art.

In comparison with these by-pass devices according to the state of the art, the device according to the invention has the remarkable following advantages:
- compactness of device;
- quick and ready filling in hydrodynamic or electrokenetic injection mode;
- lesser risk of presence of detrimental air bubbles in the device;
- lesser sensitivity to possible pressure fluctuations;
- improved particle concentrating effect because occurring in an annular continuous area located at discrete areas each defined by the rectangular cross-section of a nanochannel;
- increased optical detection threshold of fluorescent substance-laden particles, in particular for particles of biological origin and as a consequence, a greater disease diagnostic quickness;
- possibility to separate and concentrate in size particles having an initial polydispersity;
- adaptation of the height of nanochannel(s) according to the invention as a function of the liquid solution salinity.

According to the invention, the geometry of the nanochannel(s) is fixed and constant during a predetermined time period, which is an operating period for the device, that is a period during which concentration and separation, or even detection through particle fluorescence are actually made. As herein below described, the height of the nanochannel(s) can be changed when it is attempted to perform the initial device filling which enables the dedicated time to be reduced or when it is desired to separate and concentrate particles having a unit size in a different range. In other words, within the scope of the invention, the aim is not at all to make one or more nanochannels the height of which varies in operation as in a microfluidic pump.

The invention also relates to a method for operating a device for separating and concentrating particles present in a fluid just described, according to which the following steps are carried out:

a/ initially injecting a buffer liquid solution by one of the first or second microchannel;

b/ once the buffer liquid solution has reached the nanochannel, or overflows from the same, injecting the liquid solution from the other of the first or second channel.

According to an alternative, step a/ is carried out from the second microchannel and step b/ from the first microchannel.

When the injections of buffer liquid solution are made in an aerodynamic injection mode, the pressure in the first or second microchannel in which the solution is initially injected according to step a/ is preferably higher than that in the second or first microchannel respectively.

A pressure can be applied in one of the first or second microchannel and a depression is further applied in the other of the second or first microchannel, respectively.

Once step b/ is carried out and the nanochannel filled with the liquid buffer solution, preferably a step c/ of injecting a liquid containing particles to be separated and concentrated from one of the first or second microchannel is carried out, the particles having a dimension lower than the smallest height $h_3$ of the nanochannel(s) passing through the latter in order to be recovered by the other of the second or first microchannel respectively, whereas the particles having a dimension higher than the smallest height $h_3$ of the nanochannel(s) are concentrated at least partly in the peripheral portion of the first or second microchannel by which the injection according to step c/ has been made.

According to step c/, a concentration of at least one part of the particles having a dimension higher than the smallest height $h_3$ of the nanochannel(s) between two concentric nanochannels can be carried out.

According to one advantageous embodiment, a step d/ can be carried out according to which an electrical potential difference is applied between the first and second microchannels and then the step c/ of injecting from the first microchannel with fluorescent substance-laden particles is carried out.

The liquid injected in step c/ is preferably deionized water and the fluorescent substance is fluorescein.

According to this embodiment, the cap can be advantageously strained as a function of the salinity of the liquid injected in step c/.

Finally, step c/ of injecting liquid containing particles can be carried out either in a hydrodynamic injection mode or electrokinectic injection mode

BRIEF DESCRIPTION OF THE DRAWINGS

Further advantages and characteristics of the invention will become clearer upon reading the detailed description made in reference to the following figures in which:

FIGS. 5A to 5C illustrate three distinct situations of superposition or not of the Debye double layer into a fluidic nanochannel;

FIGS. 9A to 9C illustrate in a transverse cross-section view the two initial filling steps of the device according to FIG. 9;

DETAILED DESCRIPTION OF PARTICULAR EMBODIMENTS

FIGS. 1 to 8 have been discussed above in reference to prior art. Consequently, they will not be further discussed in detail hereinafter.

In the description that follows, the terms "inlet", "outlet", "upstream", "downstream" are used in reference to the direction of the liquid containing particles in a device for separating and concentrating particles according to the invention. Moreover, the terms "upper", "lower", "top", "bottom" are used in reference to the vertical physical orientation of the device according to the invention.

It is herein specified that the relative scales and proportions are not respected, for the sake of clarity of the drawings.

It is also specified that unless explicitly mentioned, the filling of devices according to the invention is described in a hydrodynamic injection mode. But all the devices according to the invention detailed hereinafter can also be filled in an electrokinetic injection mode, for example through electroosmosis or electrophoresis.

It is also specified that in all the illustrated embodiments, microchannels 1, 5, 5.1, 5.2, 5.3 are shown with a cross-section enlargement at their portions adjacent to nanochannels 3, 3.1, 3.2, 3.3. Actually, this enlargement is preferred for technological reasons related to the manufacture as better described in reference to FIGS. 17-17J. Furthermore, such enlargements advantageously enable chambers to be defined, that is increased liquid filling or particle concentrating volumes. For the sake of clarity, they are not further described in detail hereinafter.

By way of example, the following dimensions indicated in the figures can be given to the microchannels and nanochannels according to the invention:

nanochannel height $h_3$, $h_4$, $h_5$, $h_6$ ($h_3 \# h_4 \# h_5 \# h_6$): 1 to a few hundreds nm;

nanochannel width W1: 50 à 100 μm;

nanochannel width W2: 100 μm to 1 mm;

height H of the chamber portions of the microchannels: 50 to 500 μm;

cap thickness E1: a few hundreds μm.

Figure 9:
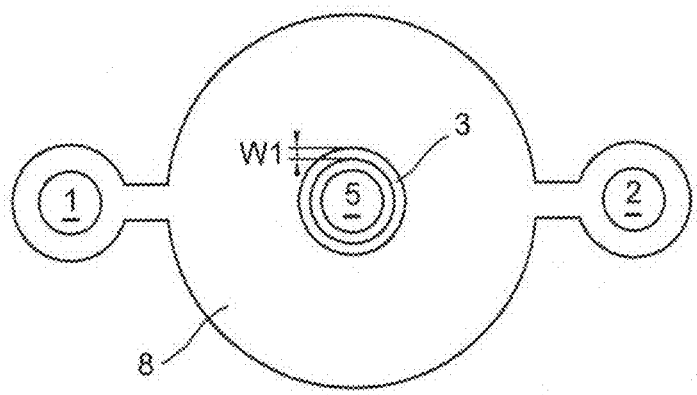
FIGS. 9 and 9A are schematic representations in top view and transverse cross-section view respectively of a first embodiment of a device for separating and concentrating particles present in a liquid according to the invention.
Figure 9A:
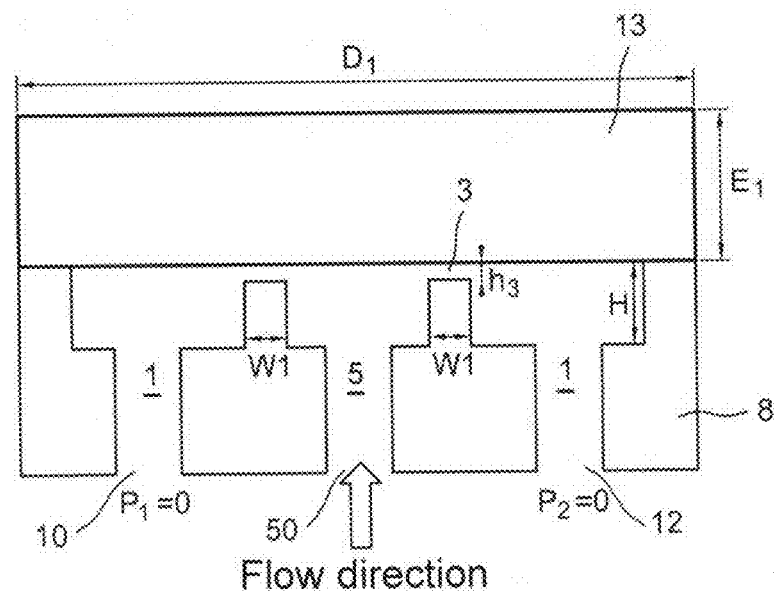

A first embodiment of the device according to the invention has been represented in FIGS. 9 and 9A.

The separating and concentrating device represented comprises a silicon substrate 8 assembled by sealing with a cap 13 of glass having a thickness E1.

They bound together a central microchannel 5 of a height H which is in fluidic communication, at its end, with a single nanochannel 3 forming a generally annular restriction of a height $h_3$ and a width w1. By end of the microchannel 5, it is meant the area of this microchannel close to the cap 13.

The nanochannel 3 is also in fluidic communication through its external periphery with a microchannel 1 having two apertures 10, 12, also of a height H which are arranged at the periphery of the device. Within the scope of the invention, the microchannel 1 can also only have a single aperture 10 or 12: in this alternative, the microchannel 5 is no longer central because actually, the microchannel 1 does not extend on either side of the microchannel 5.

To allow the subsequent particle separation and concentration thanks to the device described, it is first filled with a buffer liquid solution.

To do this, the device is placed on a fluidic bench which enables the device to be connected to a hydraulic pressure generator.

The injection of the liquid is thus made up to a pressure P5 by the central microchannel 5, the pressure in the peripheral microchannel 1 remaining null (FIG. 9A). The injection of this solution is made gradually by respecting pressure steps in order to avoid the formation of air bubbles in the central microchannel 5 to the maximum.

Figure 9B:
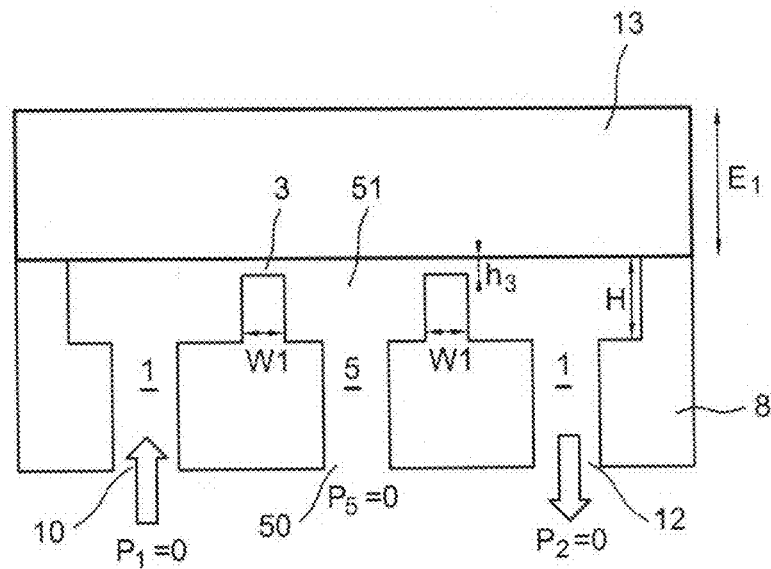

Once the liquid has reached the nanochannel 3 or overflows therefrom, an injection of the same buffer liquid is made from the microchannel 1, through one of both its apertures 10 or 12, under some pressure to completely fill the inside of the device and thus purge possible air bubbles (FIG. 9B in which the injection is made from the aperture 10 of the peripheral microchannel 1 under a pressure P1, the pressure P2 in the other aperture 12 of the peripheral microchannel being null).

The operation of the device according to the invention for separating and concentrating in sizes particles, for example microparticles or nanoparticles, is now described. Particles considered can be of biological (DNA, viruses, bacteria, cells, lipid particles, etc . . . ) or synthetic origin and be marked with a fluorophore to allow an optical detection as better described in connection with the embodiment of FIGS. 15-16A. The particles considered can be charged or electrically neutral.

Once the inside of the device is completely filled as described as above, from the single aperture 50 of the central mechanical 5, a liquid solution containing particles having an upper (Ng) and lower (Np) unit size than the height of the nanochannel 3 is directly injected. During this separating/concentrating operation, the dimensions of the nanochannel 3 are kept fixed. In other words, they are controlled.

At the end of some injection time, the particles having a unit size (Ng) higher than the nanochannel 3 are concentrated in a localized way in the chamber portion at the end 51 of the microchannel 5 where they can be detected, specially optically. Indeed, because of the restriction formed by the annular nanochannel 3, these particles are trapped in the microchannel 5, wherein they build up. Particles having a lower unit size (Np) pass through the nanochannel 3 during the entire injection and can be recovered at the outlet by either the aperture 10 or the aperture 12 of the microchannel 1 (FIG. 9C).

Figure 9C:
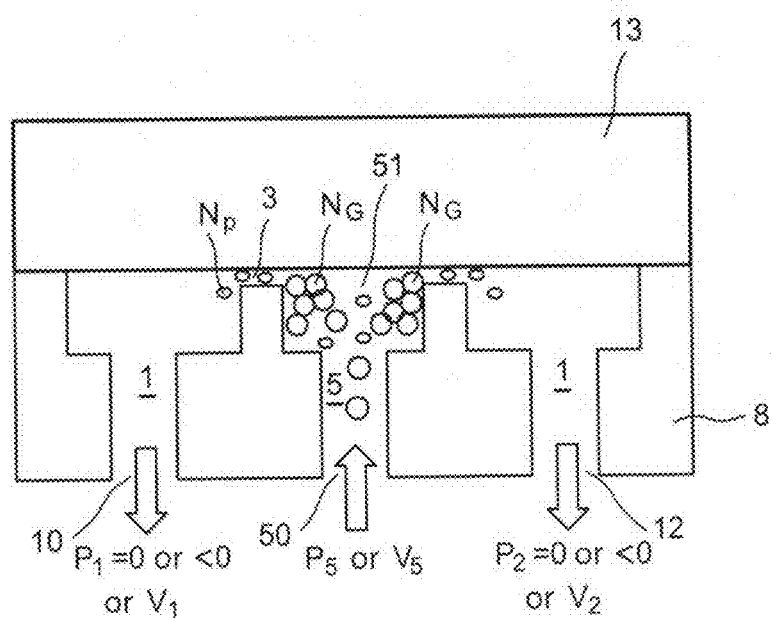

As indicated in FIG. 9C, the injection mode of the liquid solution containing particles to be separated and concentrated in size range (Ng, Np) by the central microchannel 5 can be hydrodynamic ($P_1$, $P_2$). According to this hydrodynamic injection mode, if only an overpressure is implemented, a pressure gradient must be applied between the central microchannel 5 and the peripheral microchannel 1 (P5>P1=P2). A depression can also possibly be implemented in the peripheral microchannel 1 (P1=P2 <0) to speed up the process.

Figure 1:
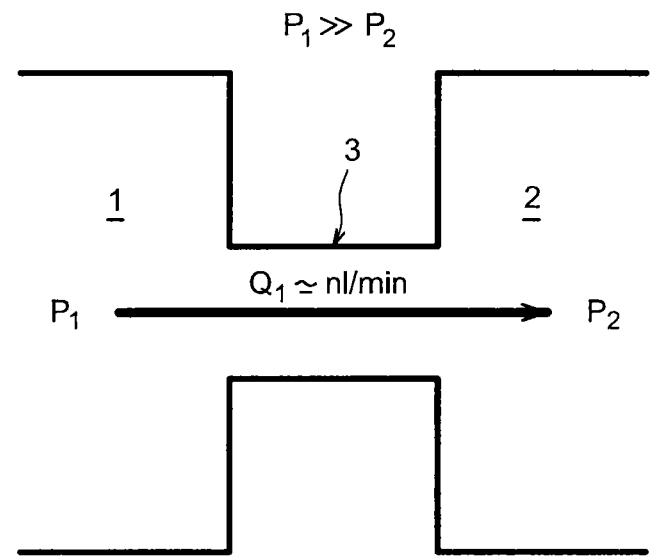
FIG. 1 is a transverse cross-section view schematic representation of a fluidic device according to the state of the art comprising a nanochannel at the junction between two microchannels.
Figure 2:
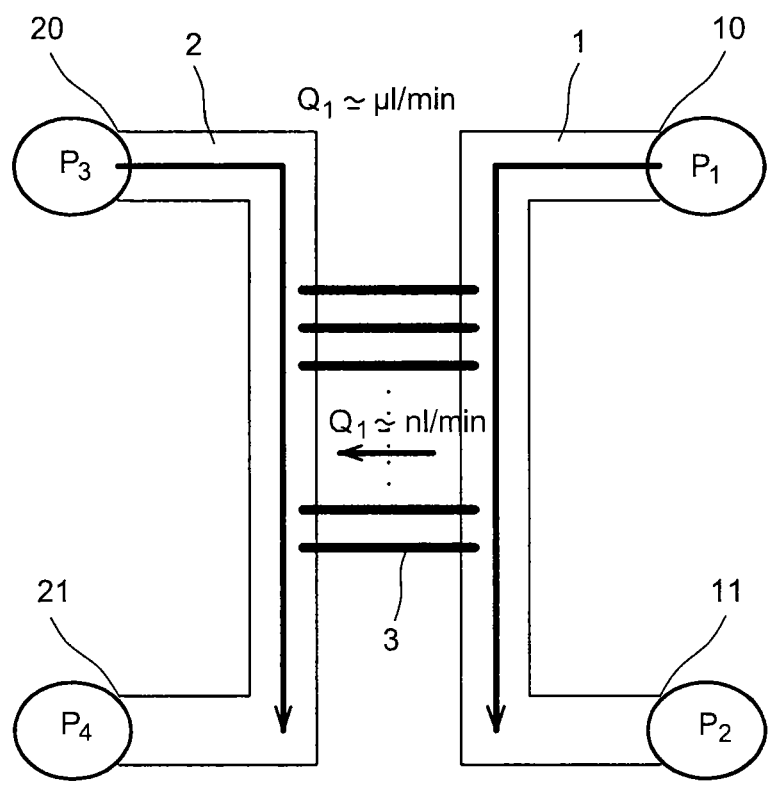
FIG. 2 is a top view schematic representation of a fluidic device according to the state of the art, of the by-pass type, comprising a plurality of nanochannels connecting two microchannels therebetween.
Figure 3:
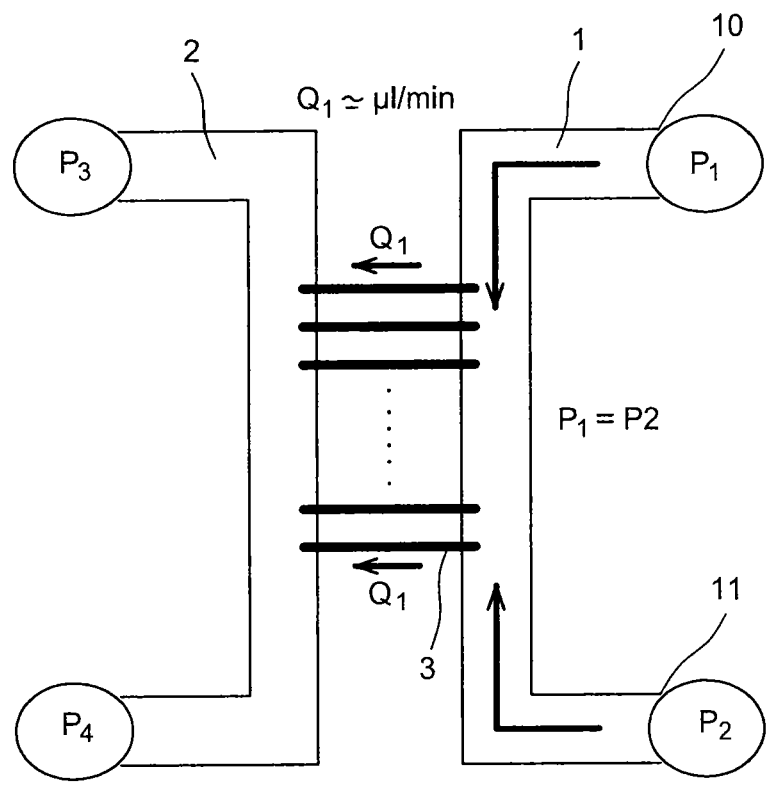
FIG. 3 is another top view schematic representation of a fluidic device according to the state of the art, of the by-pass type, comprising a plurality of nanochannels connecting two microchannels therebetween.
Figure 4:
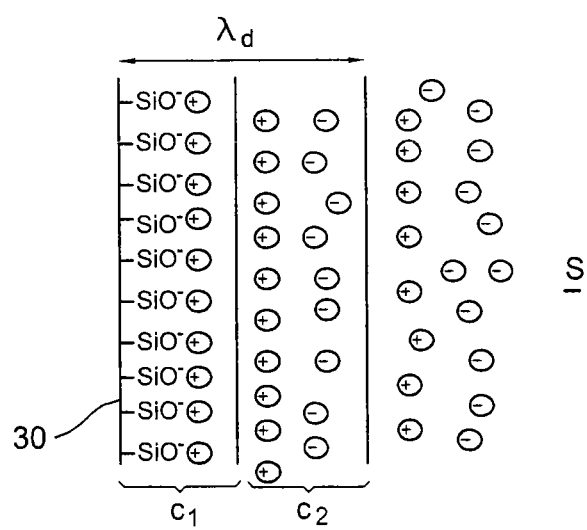
FIG. 4 is a schematic representation showing the physical phenomenon of the superimposition of Debye double layer of a buffer solution containing electrically charged species in the vicinity of an electrically charged wall.
Figure 6A:
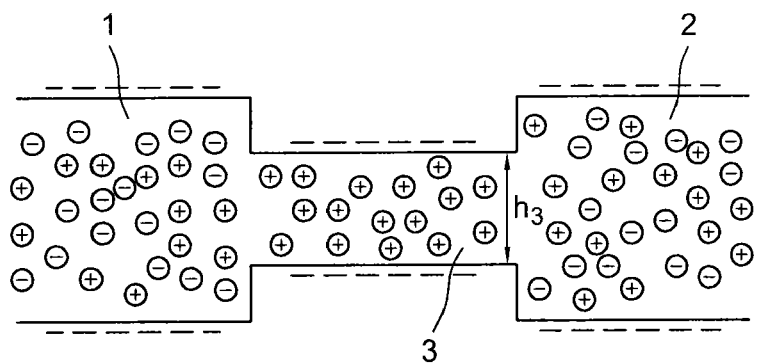
FIGS. 6A to 6D illustrate in a transverse cross-section view different steps for performing the ICP phenomenon in a fluidic device according to FIG. 1.
Figure 6B:
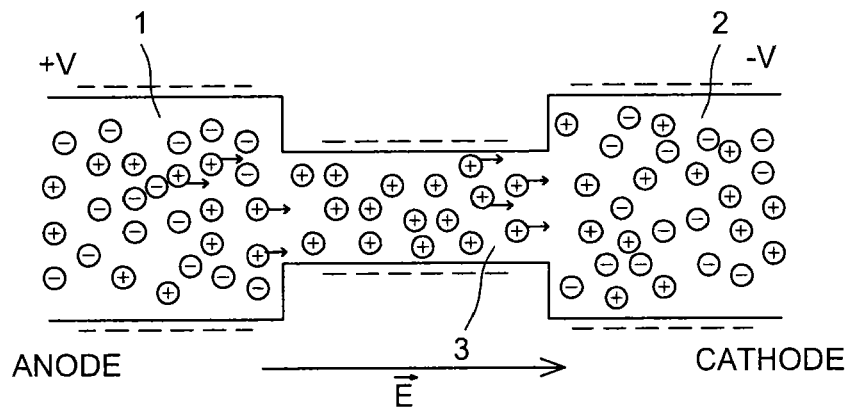
Figure 6C:
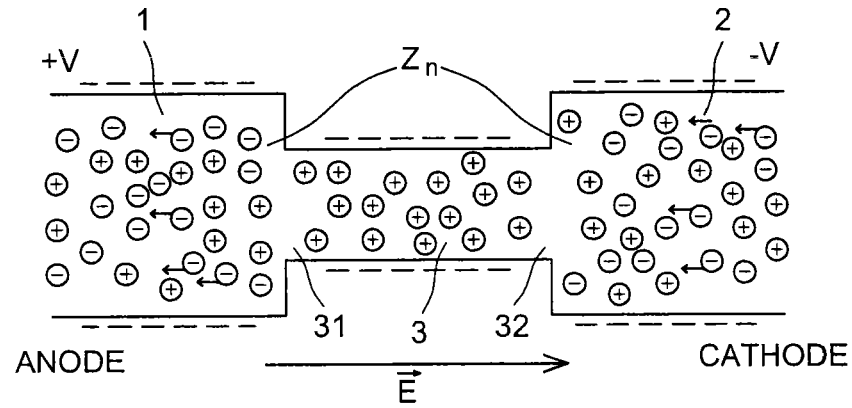
Figure 6D:
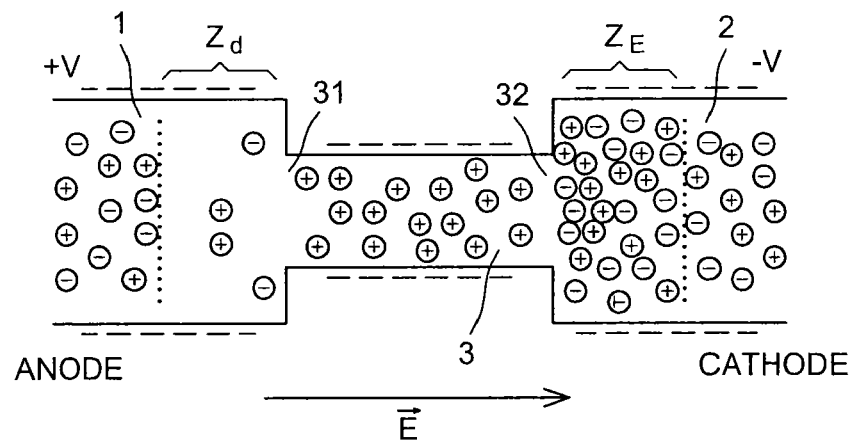
Figure 7A:
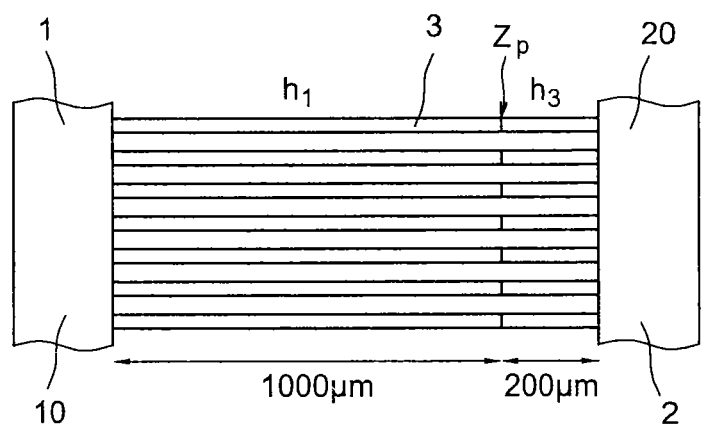
FIGS. 7A to 7B are schematic representations in top view and transverse cross-section view respectively of a by-pass fluidic device disclosed in publication [1]
Figure 7B:
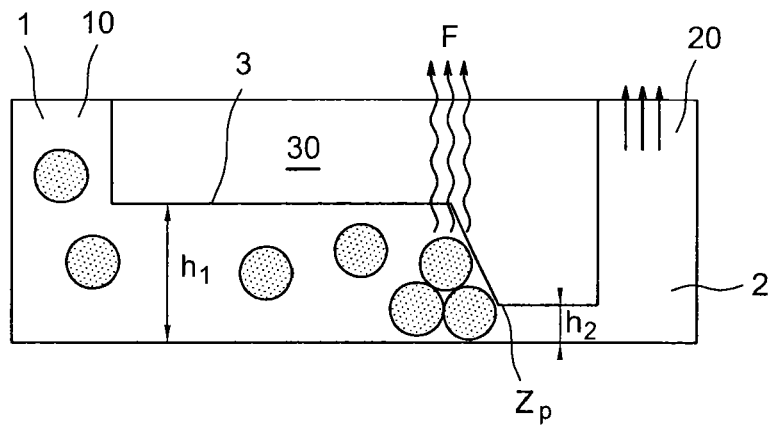
Figure 8:
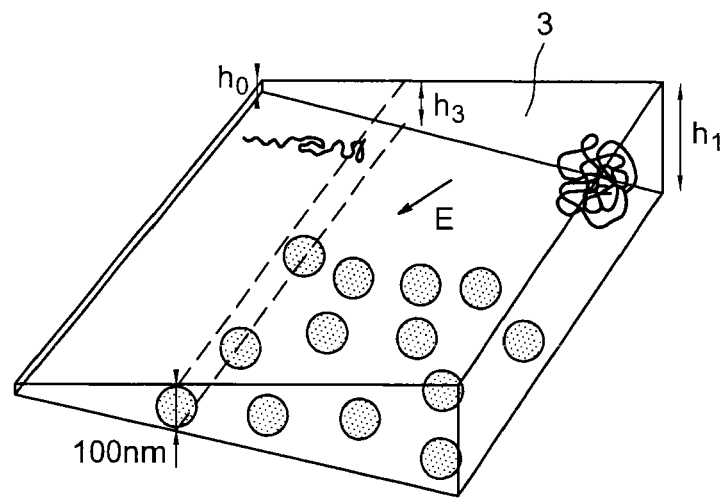
FIG. 8 is a perspective view schematic representation of a nanochannel of a by-pass fluidic device disclosed in publication [2]

By design, the central microchannel 5 of the device is less prone to pressure fluctuations than by-pass devices according to the state of the art, more particularly those described in FIGS. 2 and 3. Thus, according to the invention, by virtue of being able to concentrate particles Ng at the chamber portion of the central microchannel 5, a more stable concentrating effect can be achieved, the effect obtained being not very dependent on possible pressure fluctuations at the inlet or outlet of the device.

As an alternative, rather than perform the injection of particles through the central microchannel 5, this can also be made by one of the apertures 10 or 12 of the peripheral microchannel 1. According to this alternative, particles Np having a unit size lower than the height $h_3$ of the nanochannel 3 are recovered in the central microchannel 5 and particles Ng having a unit size higher than this height $h_3$ are concentrated at the external periphery of the nanochannel 3.

Figure 10:
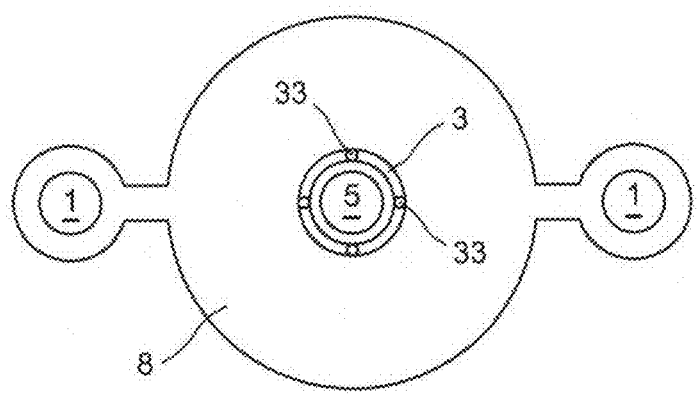
FIGS. 10 and 10A are schematic representations in top view and transverse cross-section view respectively of a first alternative embodiment of the device according to FIGS. 9 and 9A.
Figure 10A:
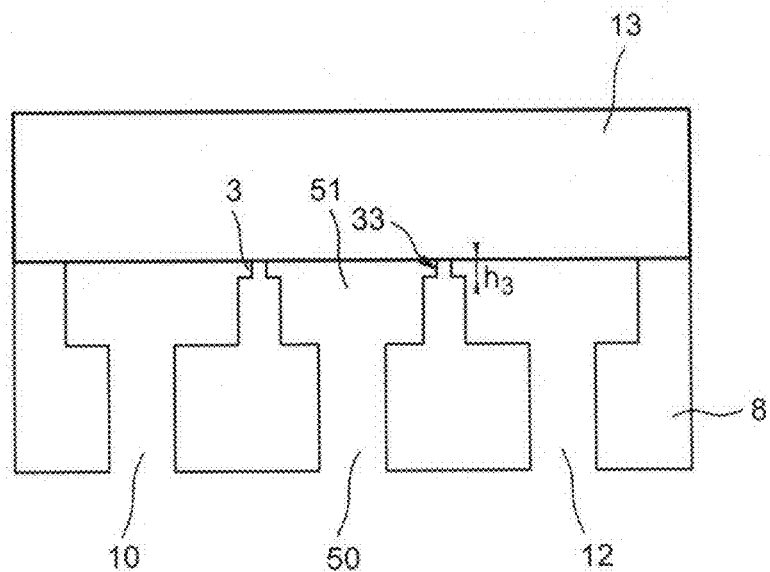

In FIGS. 10 and 10A is represented an alternative embodiment of the device just described according to which blocks 33 having the same height $h_3$ as the restriction are distributed evenly spaced in the restriction by being sealed onto the cap 13 in order to better set the height of the nanochannels 3. Here, two adjacent blocks 33 bound a nanochannel 3. Such an alternative is advantageous because it sets the height of nanochannels regardless of the pressure applied on top of the cap. In other words, the height $h_3$ of the nanochannels 3 is ensured to be kept constant regardless of the pressure which is applied to the cap 13.

Figure 11:
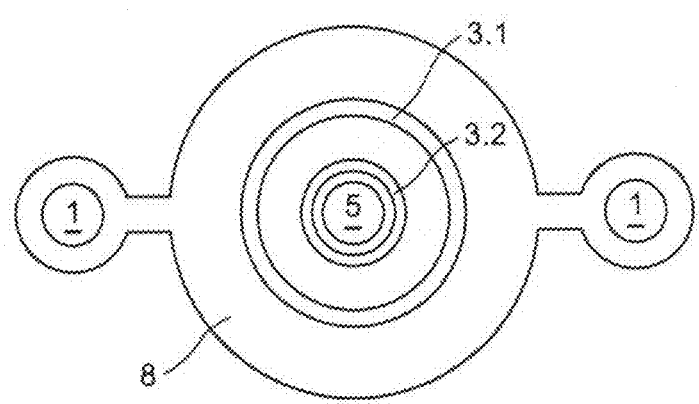
FIGS. 11 and 11A are schematic representations in top view and transverse cross-section view respectively of a second embodiment of a device for separating and concentrating particles present in a liquid according to the invention.
Figure 11A:
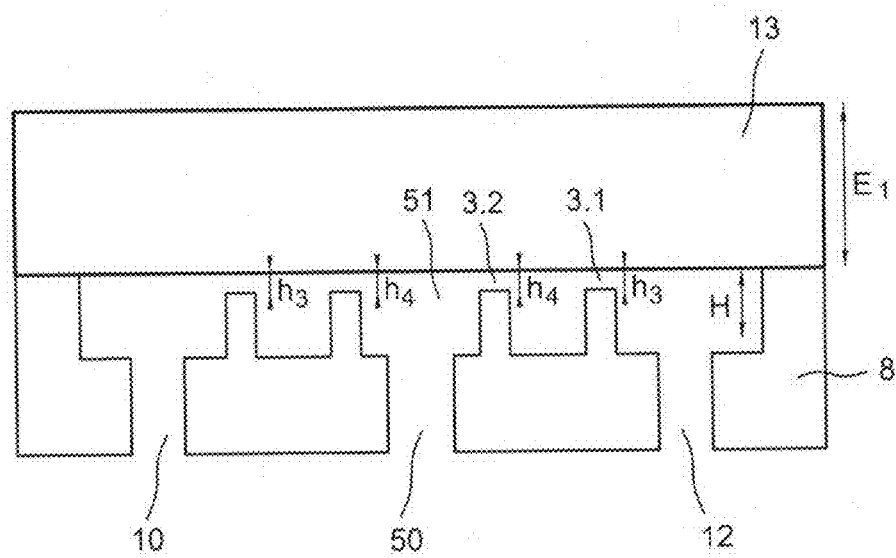

According to a second embodiment, a device according to the invention can be made with several annular nanochannels 3.1, 3.2 concentrically arranged with respect to each other and all around a central microchannel 5. The heights $h_3$, $h_4$ of the nanochannels 3.1, 3.2 can be different from each other to advantageously enable particles having a different unit size to be separated (FIGS. 11 and 11A).

Figure 12:
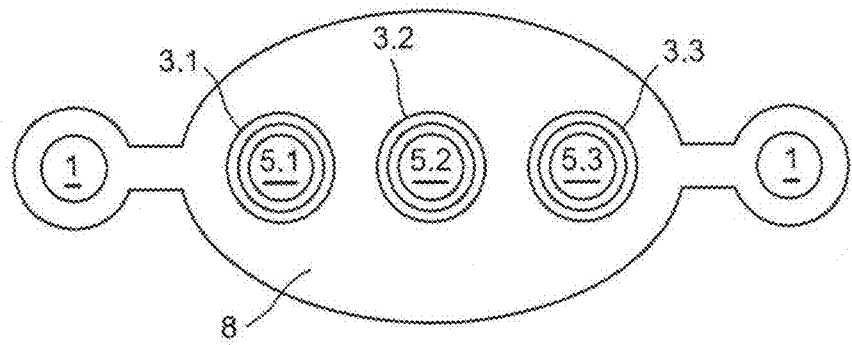
FIGS. 12 and 12A are schematic representations in top view and transverse cross-section view respectively of a third embodiment of a device for separating and concentrating particles present in a liquid according to the invention.
Figure 12A:
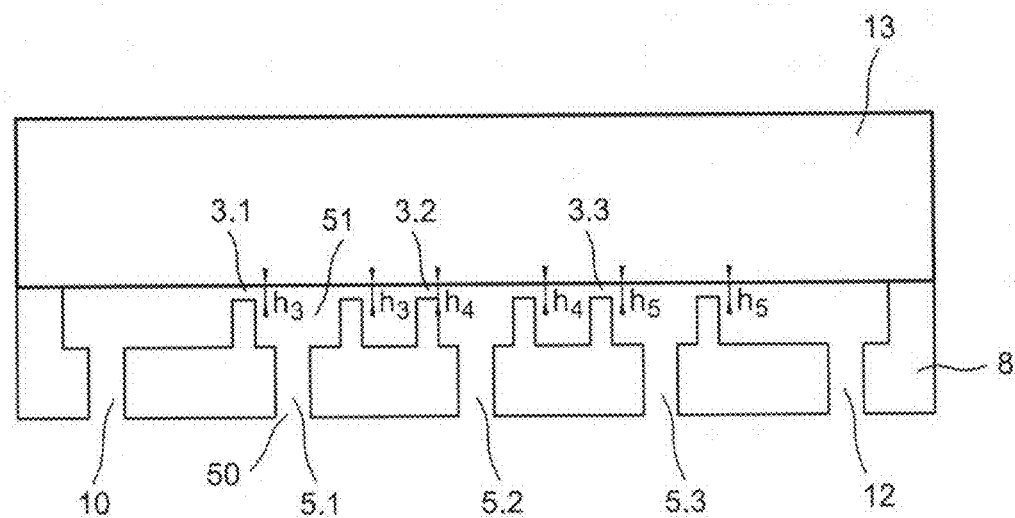

In a third embodiment, a device according to the invention can be made with several annular nanochannels 3.1, 3.2, 3.3 in hydraulic series with each other, each nanochannel 3.1, 3.2, 3.3 being arranged around a central microchannel 5.1, 5.2, 5.3. Heights $h_3$, $h_4$ and $h_5$ of nanochannels 3.1, 3.2, 3.3 can be different from each other and thus enable nanoparticles having different size ranges to be separated (FIGS. 12 and 12A). This embodiment is advantageous because by placing several nanochannels in hydraulic series, a particle separation matrix is somehow made, which allows separation at a greater scale (FIGS. 12 and 12A).

Figure 13:
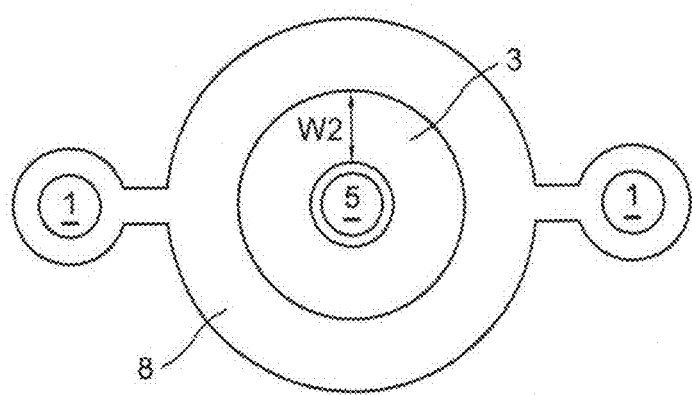
FIGS. 13 and 13A are schematic representations in top view and transverse cross-section view respectively of a second alternative embodiment of the device according to FIGS. 9 and 9A.
Figure 13A:
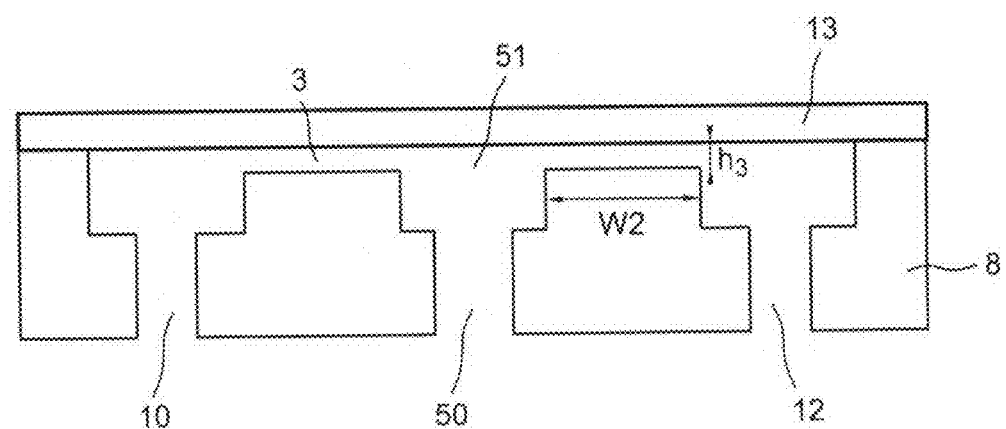
Figure 13B:
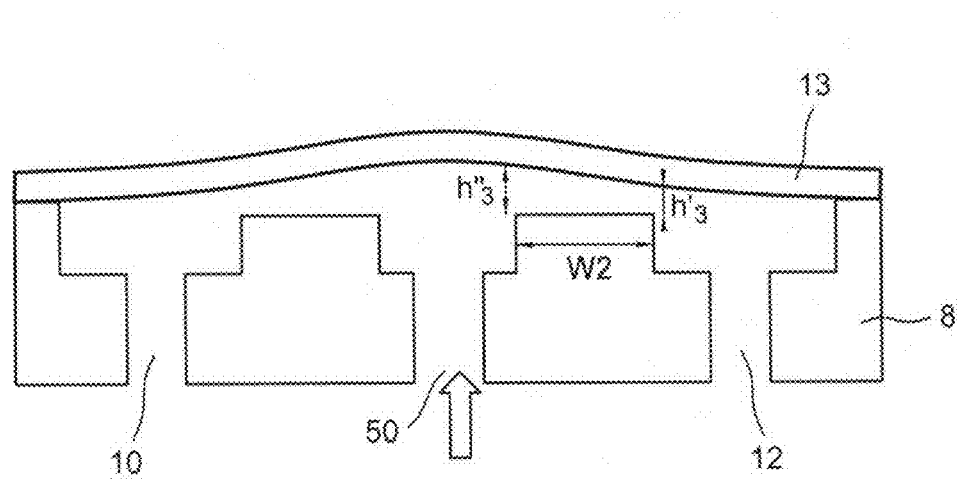
FIG. 13B shows a strained state of a cap according to FIGS. 13 and 13A.

According to a second alternative embodiment, a device according to the invention can be made with a lessened thickness E1 of the cap 13 while increasing the width W2 of the microchannel (3) formed between the microchannel 5 and the microchannel 1. This allows the cap 13 to be rendered flexurally strainable when a pressure is applied to the cap under the action of an actuator (FIGS. 13 and 13A). Thus, a height gradient of the nanochannel 3 can be created by flexurally straining the cap 13. This height gradient ($h_3'$ to $h_3''$) can be used advantageously to separate particles having a different unit size (FIG. 13B). Thus, with a flexurally strainable cap 13, depending on the more or less high pressure applied in the central microchannel 5, the cap 13 is more or less strained and a more or less high height gradient is generated (gradient decreasing from $h_3''$ to $h_3'$ in FIG. 13B). Such an alternative is advantageous because during a same operation, particles having different unit sizes can be separated by simply modulating the pressure applied to the cap. One can thus have a strainable glass cap having a low thickness E1 with a roughness in the order of a few angstroms. It is worthy of note that according to this second alternative, resorting to the actuator enables the strain of the cap to be controlled, such that the geometry of the nanochannel (3), separating the microchannel 5 from the microchannel 1, is fixed during a determined time period.

Figure 14:
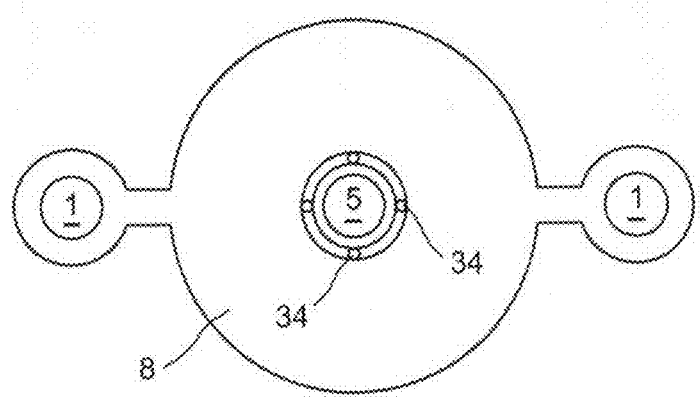
FIGS. 14 and 14A to 14B are schematic representations in top view and transverse cross-section view respectively of a third alternative embodiment of a device according to FIGS. 9 and 9A.
Figure 14A:
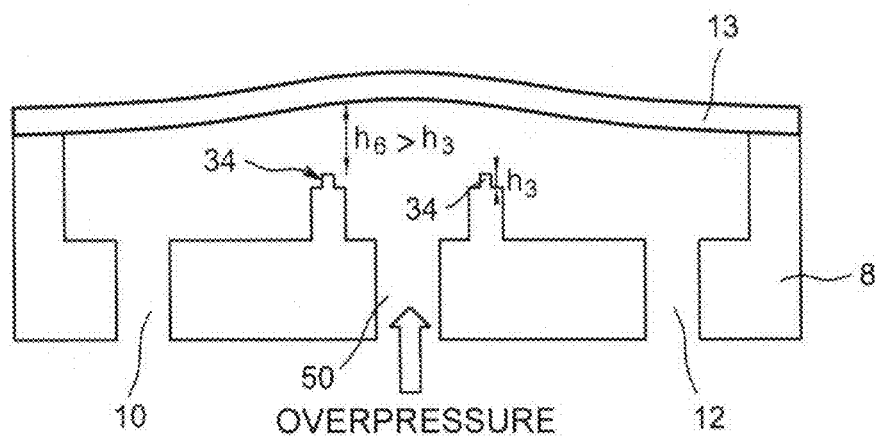
Figure 14B:
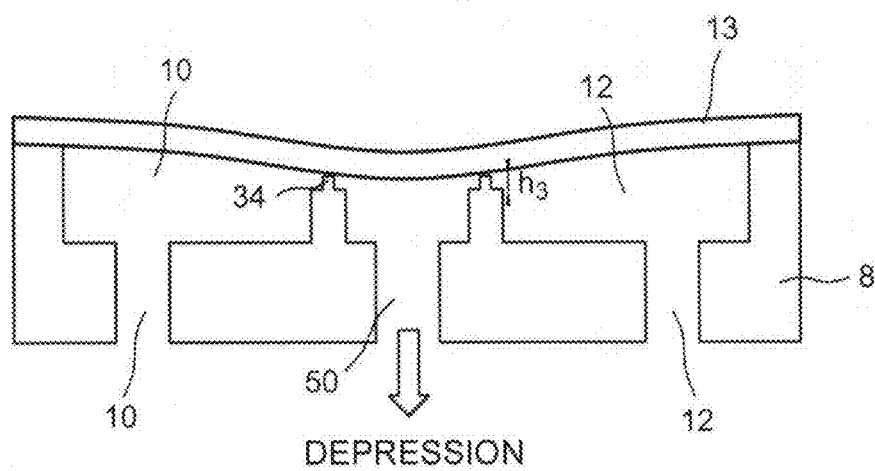

In a third alternative embodiment, a device according to the invention can be made with a strainable cap 13 and blocks 34 having a height $h_3$ lower than the height of the restriction 3 of annular geometry. Here, two adjacent blocks 34 form a nanochannel 3, each nanochannel separating a microchannel 5 from a microchannel 1. These blocks 34 are made during the manufacture better described in connection with FIGS. 17-17J and are not sealed to the cap 13. These blocks 34 act as stops to control the height of the nanochannels 3 when a stress is applied to the cap 13 (FIGS. 14A and 14B). Thus, during a time period corresponding to the separating/concentrating operation, the height of the channel remains fixed and constant. This stress can be a mechanical stress to the cap 13 or a depression for example in the central microchannel 5. Thanks to this strain of the cap 13, advantageously of glass having a low thickness, the device can thus be initially more easily filled from the central microchannel 5 and air bubbles that can be trapped at the central microchannel 5 can thus be purged. Once the initial filling is performed, a depression can be applied in the central microchannel 5. A separation (filtration) is thus achieved of nanoparticles Np having a size lower than the height of nanochannels which is maintained fixed and constant thanks to the blocks 34, these particles passing through the nanochannels 3, as well as a concentration of particles having an upper unit size Ng at the external periphery of the nanochannels 3.

In the alternatives of FIGS. 13 and 14B, the flexural strainability of the cap 13 allows a device according to the invention with a greater operational flexibility in terms of filling and size ranges of particles to be separated. Indeed, in these alternatives, the height of nanochannels forming the restriction of annular geometry can be made variable both in space and time. As already specified, the actuator enabling the flexural strainability of the cap 13 to be achieved can be an actuator attached to the latter, such a piezoelectric element, or can be as well the fluid itself inside the device, for example the depressurized fluid in the microchannel 5 or the overpressurized in the microchannel 1.

Figure 15:
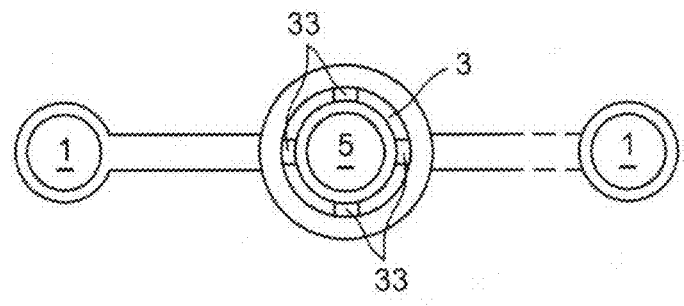
FIGS. 15 and 15A are schematic representations in top view and transverse cross-section view respectively of a fourth embodiment of a device for separating and concentrating particles present in a liquid according to the invention.
Figure 15A:
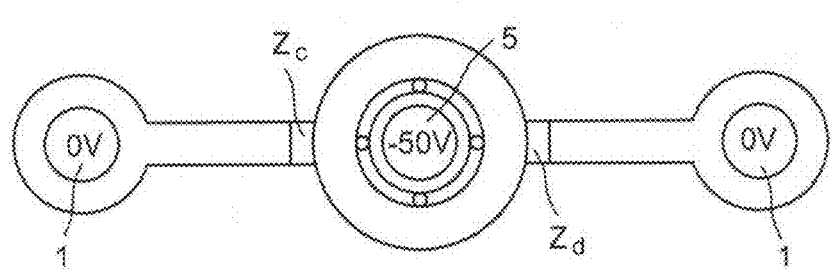

In the fourth embodiment of FIGS. 15 to 15A, the ICP physical principle is implemented in a device according to the invention. This principle with different notations have already be given in the preambule of this application.

A device according to FIGS. 10 and 10A is herein used: the height $h_3$ of nanochannels 3 forming a restriction of annular geometry is thus maintained fixed and constant using silicon blocks 33 sealed to the glass cap 13.

In this embodiment, for example, a fluorescein solution diluted in deionized water is injected through the central microchannel 5. When the solution fills the nanochannel 3 and overflows in a peripheral microchannel 1, the entire device is filled via the latter microchannel 1. Then, using an electrical voltage generator, a potential difference is applied between the central microchannel 5 and the peripheral microchannel 1 and the depletion areas Zp and concentration area Zc of fluorescein-laden species are observed. And then, a gradual pressure is applied from the peripheral microchannel 1 (FIG. 15A).

More precisely, using an epilfluorescent optical microscope, the concentrating effect of fluorescein by the ICP phenomenon has been observed, in connection with FIGS. 15A, 15B, 16A-16C.

First, a fluorescein solution diluted in deionized water is injected through the central microchannel 5 by applying a pressure up to a value of 1 bar approximately. The gradual injection enables to have as few air bubbles as possible inside the device.

Figure 16A:
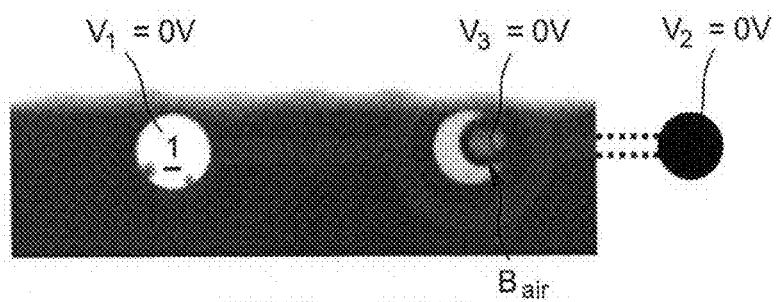
FIGS. 16A to 16C are photographic reproductions of the device at different operating times according to FIGS. 15 and 15A.
Figure 16B:
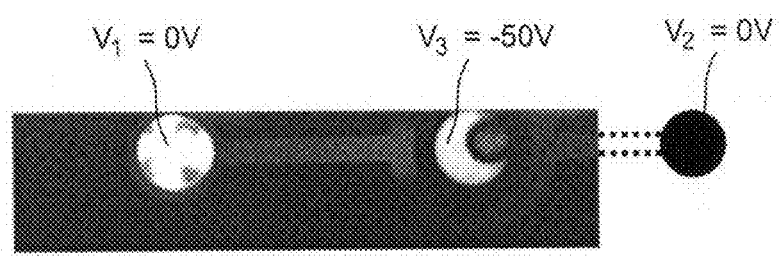

At this time, all the electrical potentials $V_1$, $V_2$, $V_3$ of the microchannels 1 and 5 are null (FIG. 16A).

Then, a suitable electrical potential is applied to generate a depletion area. Typically, electrical potentials in the peripheral microchannel 1 are null (potentials in the apertures 10 and 12: $V_1=V_2=0V$) whereas the electrical potential of the central microchannel 5 is brought to $V_3=-50V$. Since the fluorescein is negatively charged, it is repelled as the depletion area is enlarged at the external periphery of the nanochannels 3. The dark area seen in FIG. 16B at the nanochannels 3 corresponds to the ionic depletion area which begins extend.

Figure 16C:
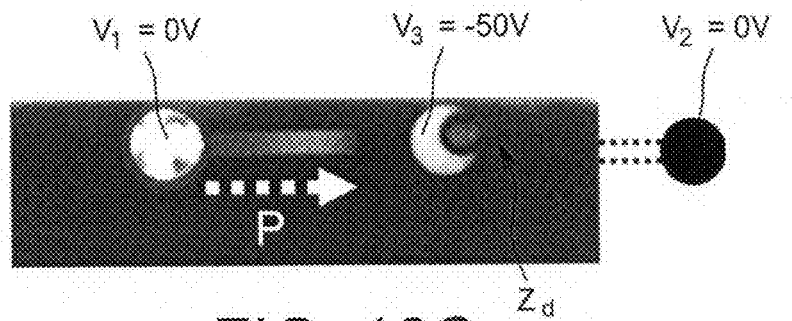

A gradual pressure of a few mbar is then applied to the deionized water from the peripheral microchannel 1. An increase in fluorescence is then observed at the electrostatic barrier created by the depression area Zd, which shows a concentrating effect (FIG. 16C).

As already indicated above, it is possible to vary the height of nanochannels 3 in time and space within a same device. This provides greater operational flexibility in particular in relation to the salinity of the liquid solution injected to obtain the ICP physical phenomenon. Indeed, if the solution is hardly salted, a height $h_3$ of nanochannels 3 of about 100 nm is allowed because in this case, thicknesses of Debye double layers in the one or more nanochannels 3 are substantially of the same order of magnitude. The superimposition of the same with the nanochannel(s) can thus be made to achieve the ionic selective permeability as shown in FIG. 5C and thus achieve the ICP phenomenon. On the other hand, for a very salted solution, it is preferable to strain the cap 13 such that the height $h_3$ of the restriction formed by the nanochannel(s) 3 is lower and the ICP phenomenon is more easily generated.

Thus, for the duration of the ICP phenomenon, the channel height should be maintained constant.

To flexurally strain the cap 13 on demand, an electromechanical actuator, such as a piezoelectric element, can be advantageously attached to the upper face of the cap 13. This can thus be oscillated in real time and on demand, and in the embodiment where the ICP phenomenon is attempted to be obtained, the depression area Zp can thus oscillate over time.

Figure 17:
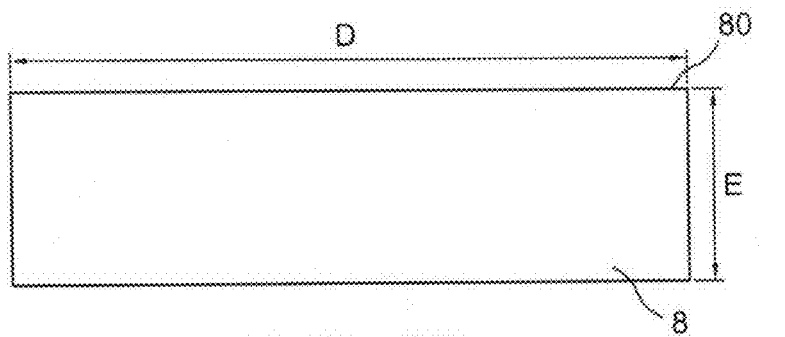
FIGS. 17 to 17J illustrate in a transverse cross-section view different steps for manufacturing a device for separating and concentrating particles present in a liquid according to the invention.
Figure 17A:
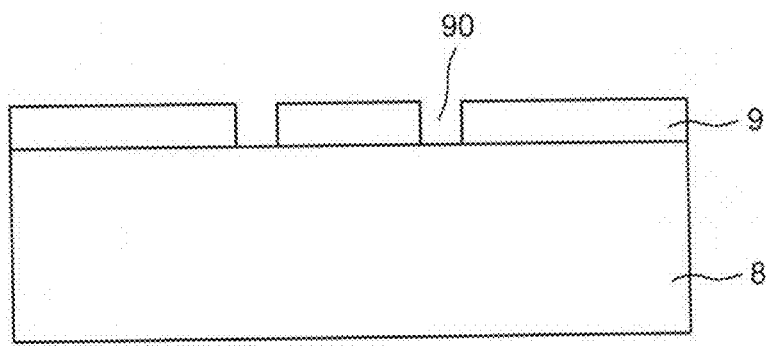
Figure 17B:
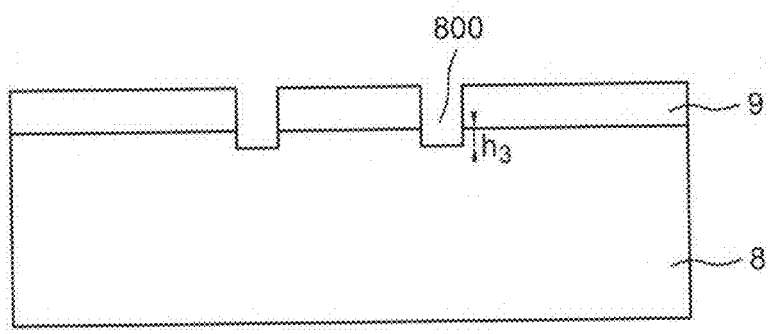
Figure 17C:
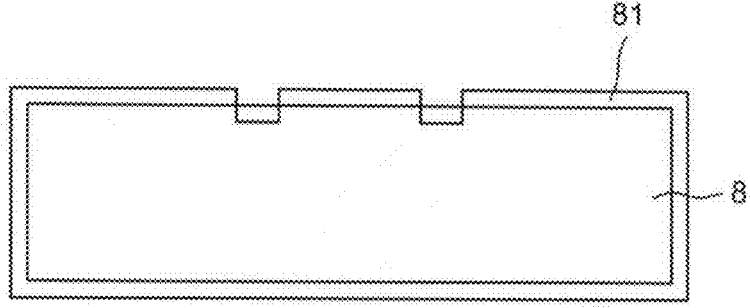
Figure 17D:
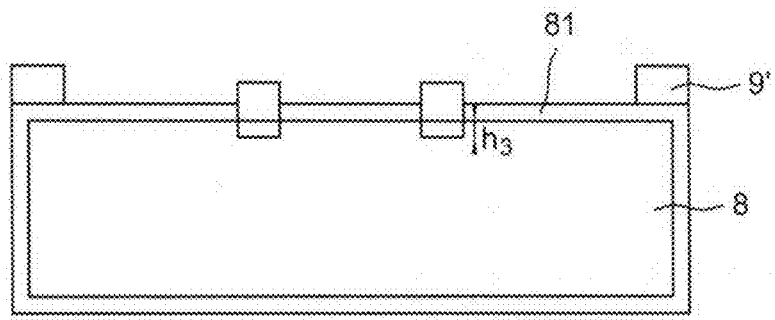
Figure 17E:
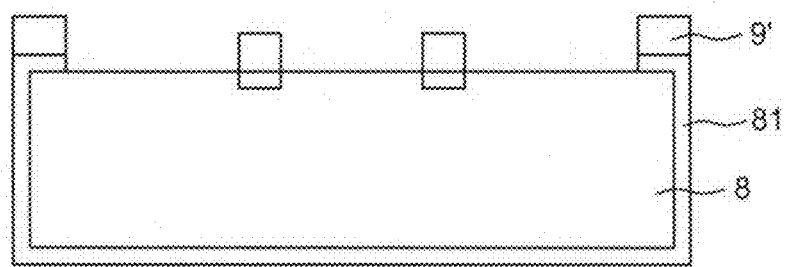
Figure 17F:
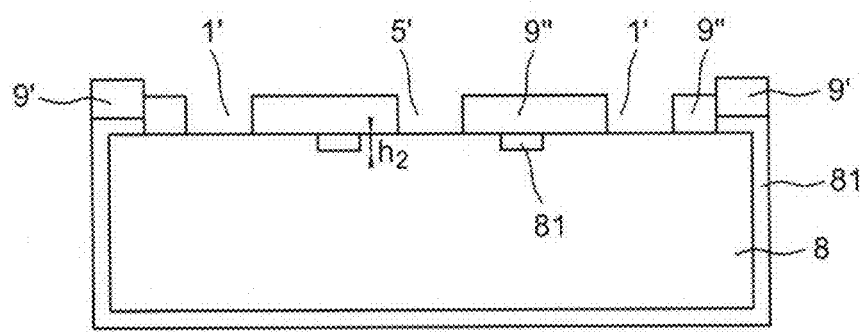
Figure 17G:
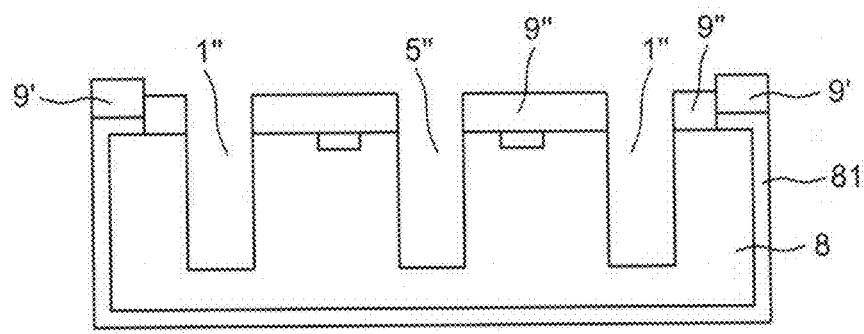
Figure 17H:
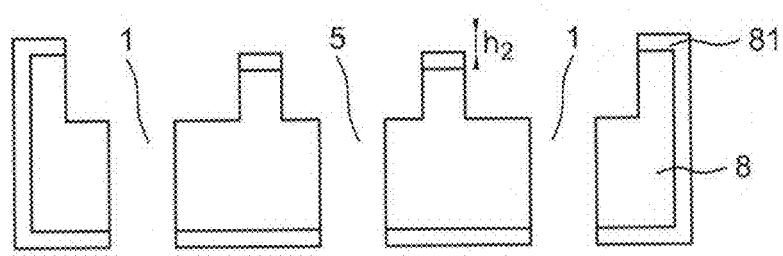
Figure 17I:
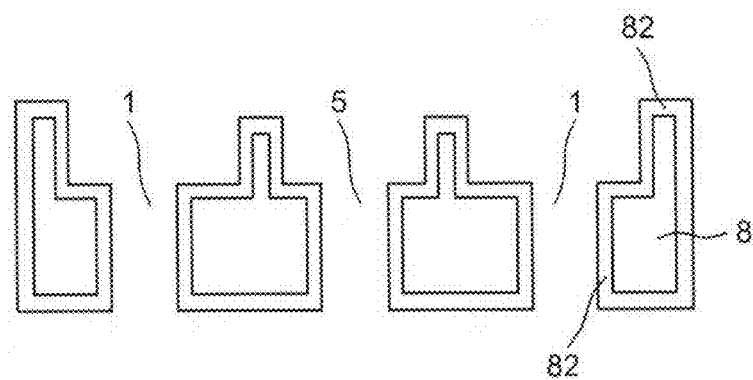
Figure 17J:
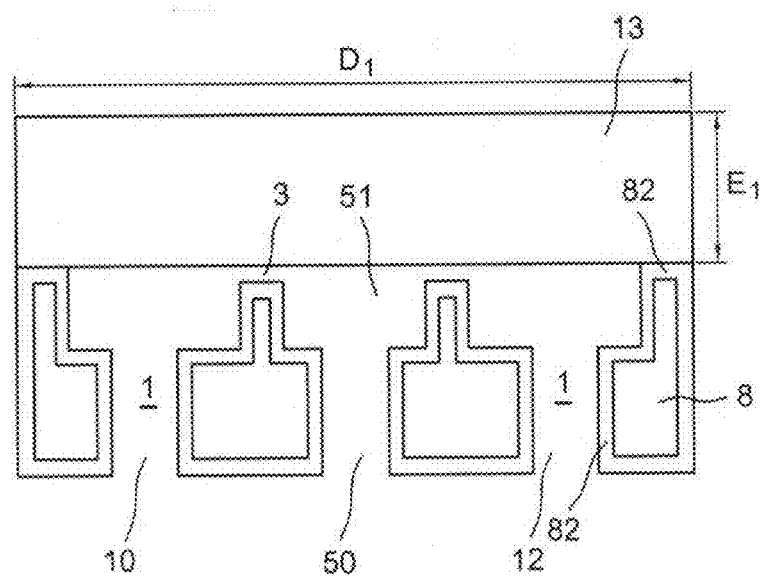

It has been represented in FIGS. 17-17J the different steps of a method for manufacturing a device for separating and concentrating particles according to the invention, more exactly the one represented in FIGS. 9 and 9A.

First, there is a first substrate 8 formed, for example, from a polished silicon plate. Typically, this is a silicon "wafer" of a diameter D equal to 100 mm and of a thickness E in the order of 500 µm (FIG. 17).

Then, a first photolithography step is performed: first, a positive photoresist layer 9 having a low thickness is deposited onto the upper face 80 of the first substrate 8, and then it is exposed to a light radiation to define the generally annular shaped pattern 800 of the nanochannel 3 finally created (FIG. 17A).

Then, a first reactive ion etching (RIE) step is performed, of the first substrate 8, for a time of about ten seconds at a desired height $h_2$ to structure the nanochannel 3, wherein this height $h_2$ can be between 50 and 500 nm (FIG. 17B).

Then, a first thermal oxidation step is performed on the first substrate 8, typically at a temperature between 800° C. and 1200° C., and a hard silica mask 81 is obtained (FIG. 17C).

Then, a second photolithography step is performed: a positive photoresist layer 9' having a low thickness is first deposited onto the upper face 80 of the first substrate 8, and then it is exposed to a light radiation to define the pattern covering the annular pattern 800 of the nanochannel 3 finally created and the periphery of the upper face of the first substrate 8 (FIG. 17D).

Then, a second RIE etching step is performed for structuring the hard silica mask 81 required for etching finally created microchannels. In other words, the portions of the hard mask 81 which are not covered by the resin 9' are removed by this second RIE etching step (FIG. 17E).

Then, a third photolithography step is conducted, first a positive photoresist layer 9" having a low thickness is deposited onto the upper face 80 of the first substrate 8, and then it is exposed to a light radiation to define a pattern defining fluidic apertures (FIG. 17F).

Then, a deep reactive-ion etching (DRIE) is performed, on the first substrate 8 to create the apertures of the microchannels. In other words, blind holes 1", 5" are created in the thickness of the first substrate 8 (FIG. 17G).

Then, a second and last DRIE dry etching step is performed to finally etch the microchannels 1, 5 and make them open into either side of the first substrate 8 (FIG. 17H).

Then, a second and last thermal oxidation step is performed for the first substrate 8 in order to define a hard silicon oxide layer 82 covering the entire surface of the first substrate 8 and which thereby ensures electric insulation of all the fluidic channels (nanochannel 3 and microchannels 1, 5) (FIG. 17I).

The upper face of the device according to the invention is then sealed by a molecular sealing technique with a second cap forming substrate 13, of glass having a low thickness (FIG. 17J). Typically, the glass cap 13 has a diameter D1 of 100 mm and a thickness E1 in the order of 500 µm. The thickness E1 of the cap 13 can even be lower than 200 µm in order to be flexurally strainable and thus enabling as explained above either a quicker filling of the fluidic channels by "broadening" temporarily the nanochannel 3, or a change over time in the height of the nanochannel 3 to obtain an ICP phenomenon differentiated over time.

It goes without saying that when it is desired to have a device according to the invention with block forming extra heights only acting as spacers 33 sealed to the cap 13 (FIG. 10A) or acting as stops 34 not sealed to the cap 13 to ensure the abutment of the latter in strain (FIGS. 14A and 14B), it is planned to perform the manufacturing steps just described accordingly.

Other embodiments or alternatives can be contemplated without departing from the scope of the invention.

Thus, if a first silicon substrate 8 has been described for manufacturing a device according to the invention, this can also be a glass, plastic substrate . . .

Furthermore, if a second glass substrate 13 has been described for manufacturing the device according to the invention, this can be a polydimethylsiloxane (PDMS) cap.

Moreover, even if this has not been described in the detailed description, the annular portion can be functionalized at the end 51 of the central microchannel 5 and the portion of cap which are adjacent to the nanochannel 3 by the presence of ligands secured at their surface by a silylated function in order to capture particles concentrated at said portions. In other words, within the device according to the invention, a particle capture area by functional sites, such as antibodies, can be implemented. Silylated functions which are perfectly suitable to somewhat provide the DNA chip function to the device according to the invention, are those described in patent application WO 2008/006871 on behalf of the applicant.

Even though the detailed cases describe a device comprising a microchannel 1 with several fluidic inlets 10, 12, this microchannel can have only a single inlet, with the resulting drawback of a higher pressure loss, since the entire fluid introduced into the microchannel having to pass through the nanochannel.

References Cited

[1]: Mark N. Hamblin et al, Department of Electrical and Computer Engineering, Brigham Young University, USA: "*Selective trapping and concentration of nanoparticles and viruses in dual-height nanofluidic channels*";

[2]: Samuel M. Stavis et al, National Institute of Standards and Technology—Semiconductor Electronics Division, USA: "*Nanofluidic structures with complex three-dimensional surfaces*".

The invention claimed is:

1. Device for separating and concentrating particles present in a fluid, comprising:
   a first microchannel, having at least one first aperture;
   at least one second microchannel, having at least one second aperture, and an end, wherein
   the first microchannel extends along a line which circumscribes the second microchannel such that the first microchannel surrounds at least part of the second microchannel at said end;
   the first microchannel and the second microchannel are connected, at said end, by at least one nanochannel, the nanochannel(s) forming a restriction between the first microchannel and the second microchannel, the geometry of which is fixed during a predetermined time period; and
   a cap bounding the first microchannel, the second microchannel and the nanochannel at said end, the first microchannel and the second microchannel being made in a first substrate, said first aperture and said second aperture opening into a same face of this substrate.

2. Device according to claim 1, wherein the cap is made in a second substrate, assembled with the first substrate, the nanochannel being bounded by a space between the first and second substrates.

3. Device according to claim 1, wherein the first microchannel has two first apertures.

4. Device according to claim 3, wherein the second microchannel has a single second aperture.

5. Device according to claim 1, wherein the restriction between the first and second microchannels is spatially distributed according to a closed annular or polygonal geometry, the connection between the first and second microchannels being made by the one or more nanochannels distributed according to this geometry.

6. Device for separating and concentrating particles present in a fluid according to claim 5, further comprising a plurality of block-forming extra heights distributed evenly spaced inside the restriction such that said one or more nanochannel comprises multiple nanochannels, said blocks being of a height $h_3$ at most equal to that of the restriction, two adjacent blocks bounding a nanochannel.

7. Device for separating and concentrating particles present in a fluid according to claim 6, wherein the blocks are of height $h_3$ substantially equal to that of the restriction formed by the nanochannels and are sealed to the cap and thus make up sealing blocks.

8. Device for separating and concentrating particles present in a fluid according to claim 6, wherein the blocks are of height $h_3$ lower than that of the restriction formed by the nanochannels and are not sealed to the cap.

9. Device for separating and concentrating particles present in a fluid according to claim 1, wherein the cap is adapted to be capable of being flexurally strained under the action of an actuator, while being kept fixed during a determined time period.

10. Device for separating and concentrating particles present in a fluid according to claim 9, wherein at least one electromechanical actuator is attached to an upper face of the cap to flexurally strain it.

11. Device for separating and concentrating particles present in a fluid according to claim 10, wherein the electromechanical actuator is a piezoelectric element.

12. Device for separating and concentrating particles present in a fluid according to claim 1, comprising at least two restrictions, formed by the one or more nanochannels, having a closed annular or polygonal shape, concentrically arranged one with respect to one another around a single second microchannel.

13. Device for separating and concentrating particles present in a fluid according to claim 12, wherein a height $h_3$ of one of both restrictions formed by the one or more nanochannels is different from a height $h_4$ of the other of both restrictions formed by the one or more nanochannels.

14. Device for separating and concentrating particles present in a fluid according to claim 1, comprising at least two second microchannels and at least two restrictions, formed by the one or more nanochannels, having a closed annular or polygonal shape, or part of it, part or all of each nanochannel being arranged around a single second microchannel.

15. Device for separating and concentrating particles present in a fluid according to claim 14, wherein a height $h_3$, $h_4$ or $h_5$ of one of both nanochannels is different from the height $h_3$, $h_4$ or $h_5$ of the other of both nanochannels.

16. Device for separating and concentrating particles present in a fluid according to claim 1, wherein the portion at the end of the second microchannel and the portion of the cap adjacent to the nanochannel are functionalized by the presence of ligands secured to their surface by a silylated function in order to capture particles concentrated at said portions.

17. Method for operating a device for separating and concentrating particles present in a fluid according to claim 1, using the device of which the following steps are carried out:
   a/ initially injecting a buffer liquid solution into one of the first or second microchannel;
   b/ once the buffer liquid solution has reached the nanochannel, or overflows from the nanochannel, injecting the buffer liquid solution into the other of the first or second microchannel.

18. Method for operating a device for separating and concentrating particles present in a fluid according to claim 17, wherein step a/ is carried out from the second microchannel and step b/ from the first microchannel.

19. Method for operating a device for separating and concentrating particles present in a fluid according to claim 17, wherein the injections of the buffer liquid solution are made in an hydrodynamic injection mode, a pressure in one of the first or second microchannel wherein the buffer liquid solution is initially injected according to step a/ being higher than a pressure in the second or first microchannel respectively.

20. Method for operating a device for separating and concentrating particles present in a fluid according to claim 17, wherein a pressure is applied into one of the first or second microchannel and a depression is further applied in the other of the second or first microchannel, respectively.

21. Method for operating a device for separating and concentrating particles present in a fluid according to claim 17, wherein once step b/ is carried out and the nanochannel is filled with the buffer liquid solution, a step c/ of injecting a liquid containing particles to be separated and concentrated from one of the first or second microchannel is carried out, the particles having a dimension lower than a smallest height $h_3$ of the nanochannel(s) passing through the nanochannel in order to be recovered by the other of the second or first microchannel respectively, whereas the particles having a dimension higher than the smallest height $h_3$ of the nanochannel(s) are concentrated at least partly in a peripheral portion of the first or second microchannel by which the injection according to step c/ has been made.

22. Method for operating a device for separating and concentrating particles present in a fluid according to claim 21, wherein according to step c/, a concentration of at least one part of the particles having a dimension higher than the smallest height $h_3$ of the nanochannel(s) between two concentric nanochannels is carried out.

23. Method for operating a device for separating and concentrating particles present in a fluid according to claim 21, wherein a step d/ is carried out wherein an electrical potential difference is applied between the first and second microchannels and then the step c/ of injecting the liquid containing particles to be separated and concentrated from one of the first or second microchannel is carried out, wherein the particles are fluorescent substance-laden.

24. Method for operating a device for separating and concentrating particles present in a fluid according to claim 23, wherein the liquid containing particles injected in step c/ is deionized water and the fluorescent substance is fluorescein.

25. Method for operating a device for separating and concentrating particles present in a fluid according to claim 23, wherein the cap is strained as a function of a salinity of the liquid containing particles injected in step c/.

26. Method for operating a device for separating and concentrating particles present in a fluid according to claim 21, wherein the step c/ of injecting the liquid containing particles is carried out in an hydrodynamic injection mode or an electrokinectic injection mode.

27. The device of claim 1, wherein the nanochannel forms a restriction with an annular shape.

* * * * *